United States Patent [19]

Nepon

[11] Patent Number: 4,865,843
[45] Date of Patent: Sep. 12, 1989

[54] COMPOSITION OF MATTER FOR CONTROLLING THE URINARY BLADDER, AND METHODS OF PREPARING AND UTILIZING SAME

[76] Inventor: Juanita Nepon, 21640 12 Mile Rd., St. Clair Shores, Mich. 48081

[21] Appl. No.: 16,117

[22] Filed: Feb. 18, 1987

[51] Int. Cl.$^4$ .................. A61K 35/78; A61K 9/44; A61K 31/355

[52] U.S. Cl. ................. 424/195.1; 424/464; 514/458

[58] Field of Search ............ 424/195.1, 464; 514/458

[56] References Cited

U.S. PATENT DOCUMENTS 4,346,522  8/1982  Nakagaki ........................... 34/12
4,447,460  5/1984  Lewis et al. ....................... 426/541

OTHER PUBLICATIONS

The Dispensatory of the U.S.A., 23rd ed., 1943, pp. 1224–1225 and 1468–1469.

Primary Examiner—John W. Rollins
Attorney, Agent, or Firm—Irving M. Weiner; Joseph P. Carrier; Pamela S. Burt

[57] ABSTRACT

A composition including dried and ground edible natural corn silks and dried and ground edible natural parsley roots, the parsley roots having as an active ingredient d-alpha tocopherol, mixed together in predetermined porportions. The composition may be provided in tablet form or powdered form, and is adapted to be taken orally by persons suffering from urinary bladder dysfunction to thereby provide relief from such affliction.

10 Claims, No Drawings

COMPOSITION OF MATTER FOR CONTROLLING THE URINARY BLADDER, AND METHODS OF PREPARING AND UTILIZING SAME

BACKGROUND OF THE INVENTION

1. Field of the Invention

The present invention relates to a novel composition which is particularly adapted for the treatment of urinary bladder dysfunction related to lack of control and which may be taken orally by a person afflicted with such dysfunction to thereby provide relief. The invention also relates to methods of preparing the aforementioned composition.

2. Description of Relevant Art

As is well known in the medical field, and more particularly by persons suffering from urinary bladder dysfunction related to lack of control, the treatment of this unpleasant and often embarrassing condition has heretofore met with only minimal success. Although various known products, medications and treatments have heretofore been available for use by persons having urinary bladder dysfunction, such products, medications and/or treatments have generally proven unsatisfactory in providing effective relief for this condition.

The present invention provides a novel composition for the treatment of urinary bladder dysfunction. The novel composition in accordance with the invention comprises a mixture of dried and ground edible natural corn silks and dried and ground edible natural parsley roots, the parsley roots having as an active ingredient d-alpha tocopherol, such ingredients being mixed together in predetermined proportions to provide a highly effective composition for the treatment of urinary bladder dysfunction.

Illustrative of known methods of dehydrating root-type vegetables is disclosed in U.S. Pat. No. 4,346,522 issued in 1982 to Nakagaki entitled "DEHYDRATING METHOD FOR A ROOT VEGETABLE AND THE LIKE" and in U.S. Pat. No. 4,447,460 issued in 1984 to Lewis et al. entitled "PROCESSED VEGETABLES." The disclosures of such patents is particularly directed toward the dehydration of root-type vegetables. Neither of these patents, however, discloses or suggests combining particular substances or compounds with dried and ground roots to produce a formula for alleviating urinary bladder dysfunction.

The novel composition in accordance with the present invention is directed toward producing effective relief from urinary bladder dysfunction related to lack of control.

SUMMARY OF THE INVENTION

The present invention provides a composition which comprises as the basic ingredients thereof dried and ground edible natural corn silks and dry and ground edible natural parsley roots, the parsley roots having as an active ingredient d-alpha tocopherol, such composition being particularly useful in treatment of urinary bladder dysfunction. The corn silks and parsley roots are natural products, and d-alpha tocopherol is therefore provided in its naturally occurring form.

The proportions of corn silks are parsley roots substantially 11:1.5.

The present invention further provides a method for preparing the aforementioned composition, comprising the steps of: combining the dried and ground edible natural corn silks and the dried and ground edible natural parsley roots in predetermined amounts, mixing such mixture with water so as to form a paste, forming the paste into individual tablet-shaped portions and drying the tablets by conventional means.

Alternatively, the mixed paste may be dried in any configuration capable of being easily ground or pulverized so as to present the product in powdered form. This form is provided for persons unable or unwilling to take tablets, as the powder may be mixed with a liquid carrier for ingestion by the user.

It is a primary object of the present invention to provide a novel composition for the effective treatment of urinary bladder dysfunction which provides substantial, if not complete, relief of the pain normally experienced by persons suffering this ailment.

It is a further object of the present invention to provide such a composition which may be taken orally in convenient forms, including tablets and powders.

Other objects and details of the invention will become apparent from the following detailed description.

DETAILED DESCRIPTION OF PREFERRED EMBODIMENTS

The novel composition in accordance with the present invention includes as the basic ingredients thereof edible natural corn silks and edible natural parsley roots.

Preferably, but not necessarily, the edible natural corn silks and edible natural parsley roots are dried and ground prior to preparation by conventional techniques under controlled conditions so as to preserve all the natural elements thereof.

The active ingredient of the parsley roots, a tocopherol, is an organic substance having the composition $C_{29}H_{50}O_2$. Tocopherol, a vitamin E factor, refers to substances including molecular forms designated alpha-, beta-, gamma-, delta-, epsilon-, zeta- and eta-tocopherol. Experimental analysis has shown d-alpha-tocopherol to be the form of choice for the present invention. (Only the dextrorotatory form is usable in biological systems, although the levorotatory form is harmless and will simply pass through the system, being eliminated as waste.)

The component parts of the present invention are readily commercially available.

In accordance with the invention, the foregoing ingredients, i.e., dried and ground edible natural corn silks and dried and ground edible natural parsley are preferably, although not exclusively, combined in proportions of substantially 11:1.5. The resulting composition is effective in relieving urinary bladder dysfunction.

To prepare the composition in accordance with the invention, the principal elements, dried and ground natural corn silks, dried and ground parsley roots are combined, in the stated predetermined proportions, with water until a paste-like consistency is obtained. In one embodiment, the paste is then formed into individual table-shaped portions with a suitable mold or by other satisfactory means. The tablets are thereafter dried by conventional techniques.

Alternatively, the prepared paste may be formed into a suitable configuration, dried, and ground or pulverized until the compound becomes a powder suitable for mixing with a liquid carrier for ingestion by the user.

The tablets or powder obtained in accordance with the foregoing method are particularly useful in the treatment of urinary bladder dysfunction, and are adapted to the taken orally to substantially alleviate the pain, discomfort and embarrassment associated with this problem.

Although not specifically disclosed hereinabove, it is further contemplated that various additives or excipients may be added to the aforesaid composition as desired. Further, although the composition has been described hereinabove as provided in tablet and powdered form, it is contemplated that, if desired, the composition may be provided in other convenient forms, such as capsules or pills.

Although there have been described what are at present considered to be the preferred embodiments of the invention, it will be understood that various modifications may be made therein without departing from the spirit or essential characteristics thereof. The present embodiments are therefore to be considered in all respects as illustrative, and not restrictive. The scope of the invention is indicated by the appended claims rather than by the foregoing description.

I claim:

1. A composition for use in treating urinary bladder dysfunction, comprising:
   dried and ground edible natural corn silks; and
   dried and ground edible natural parsley roots;
   the proportions of said dried and ground edible natural corn silks and said dried and ground edible natural parsley roots are substantially 11:1.5.

2. A composition according to claim 1, wherein: said parsley roots contain naturally occurring d-alpha tocopherol as an active ingredient.

3. A composition according to claim 1, wherein:
   said composition is provided in individual tablet portions adapted to be taken orally by a user of said composition.

4. A composition according to claim 1, wherein:
   said composition is provided in a powdered form for mixing with a liquid to be taken orally by a user of said composition.

5. A composition for treating urinary bladder dysfunction, consisting essentially of
   dried and ground edible natural corn silks; and
   dried and ground edible natural parsley roots;
   said dried and ground edible natural corn silks and said dried and ground edible natural parsley roots being proportioned at substantially 11:1.5.

6. A composition according to claim 5, wherein: said parsley roots contain naturally occurring d-alpha tocopherol as an active ingredient.

7. A composition according to claim 5, wherein:
   said composition is provided in individual tablet portions adapted to be taken orally by a user of said composition.

8. A composition according to claim 5, wherein:
   said composition as provided in powdered form for mixing with a liquid to be taken orally by the user of said composition.

9. A method for preparing a composition for use in treating urinary bladder dysfunction, comprising the step of:
   combining dried and ground edible natural corn silks and dried and ground edible natural parsley roots in predetermined amounts;
   the proportions of said dried and ground edible natural corn silks and said dried and ground edible natural parsley roots being substantially 11: 1.5;
   mixing the mixture with water so as to form a paste;
   forming said paste into individual tablet-shaped portions; and
   drying said tablets.

10. A method according to claim 9, wherein:
    said parsley roots contain naturally occurring d-alpha tocopherol as an active ingredient.

* * * * *